US009554984B2

(12) United States Patent
Battaglia et al.

(10) Patent No.: US 9,554,984 B2
(45) Date of Patent: Jan. 31, 2017

(54) ORAL CARE COMPOSITIONS FOR TOPICAL APPLICATION

(75) Inventors: Alex Battaglia, La Jolla, CA (US); Eva Beim, La Jolla, CA (US)

(73) Assignee: JALEVA PHARMACEUTICALS, LLC, San Diego, CA (US)

(*) Notice: Subject to any disclaimer, the term of this patent is extended or adjusted under 35 U.S.C. 154(b) by 0 days.

(21) Appl. No.: 10/754,430

(22) Filed: Jan. 9, 2004

(65) Prior Publication Data

US 2005/0095208 A1 May 5, 2005

Related U.S. Application Data

(60) Provisional application No. 60/517,319, filed on Nov. 3, 2003.

(51) Int. Cl.
| | |
|---|---|
| *A61Q 19/00* | (2006.01) |
| *A61Q 11/00* | (2006.01) |
| *A61K 9/08* | (2006.01) |
| *A61K 31/16* | (2006.01) |
| *A61K 31/045* | (2006.01) |
| *A61K 31/21* | (2006.01) |
| *A61K 8/92* | (2006.01) |
| *A61K 9/70* | (2006.01) |
| *A61K 9/00* | (2006.01) |

(52) U.S. Cl.
CPC ............ *A61K 8/922* (2013.01); *A61K 9/0002* (2013.01); *A61K 9/70* (2013.01); *A61Q 11/00* (2013.01)

(58) Field of Classification Search
None
See application file for complete search history.

(56) References Cited

U.S. PATENT DOCUMENTS

| | | | |
|---|---|---|---|
| 3,389,049 A | 6/1968 | Frantz | |
| 3,535,421 A | 10/1970 | Widder et al. | |
| 3,538,230 A | 11/1970 | Pader et al. | |
| 3,678,154 A | 7/1972 | Widder et al. | |
| 3,689,637 A | 9/1972 | Pader | |
| 3,699,958 A | 10/1972 | Szucs | |
| 3,711,604 A | 1/1973 | Colodney et al. | |
| 3,911,104 A | 10/1975 | Harrison | |
| 3,935,306 A | 1/1976 | Roberts et al. | |
| 4,040,858 A | 8/1977 | Wason | |
| 4,307,717 A | 12/1981 | Hymes et al. | |
| 4,496,322 A | 1/1985 | Sandham et al. | 433/217 |
| 4,514,385 A | 4/1985 | Damani | |
| 4,919,837 A | 4/1990 | Gluck | |
| 4,931,279 A | 6/1990 | Bawaet et al. | |
| 4,954,487 A * | 9/1990 | Cooper et al. | 514/159 |
| 5,063,065 A | 11/1991 | Bazterrica et al. | |
| 5,116,603 A | 5/1992 | Friedman | |
| 5,160,737 A * | 11/1992 | Friedman et al. | 424/401 |
| 5,167,649 A | 12/1992 | Zook | |
| 5,178,870 A | 1/1993 | Schaeken et al. | |
| 5,234,342 A | 8/1993 | Fischer | |
| 5,395,241 A * | 3/1995 | Kandelman | 433/217.1 |
| 5,422,100 A | 6/1995 | Eliaz et al. | |
| 5,429,590 A | 7/1995 | Saito et al. | |
| 5,438,076 A * | 8/1995 | Friedman et al. | 514/772.6 |
| 5,446,070 A | 8/1995 | Mantelle | |
| 5,456,745 A | 10/1995 | Roreger et al. | |
| 5,470,563 A | 11/1995 | Tanaka et al. | |
| 5,639,310 A | 6/1997 | Giampaolo | |
| 5,644,049 A | 7/1997 | Giusti et al. | |
| 5,759,038 A * | 6/1998 | Fischer | 433/215 |
| 5,760,052 A | 6/1998 | Peacock | |
| 5,763,412 A | 6/1998 | Khan et al. | |
| 5,776,430 A | 7/1998 | Osborne et al. | |
| 5,942,239 A | 8/1999 | Huprich et al. | |
| 6,143,794 A | 11/2000 | Chaudhuri et al. | |
| 6,228,354 B1 | 5/2001 | Jeng | |
| 6,379,673 B1 | 4/2002 | Diwan | |
| 6,676,952 B2 | 1/2004 | Renimel | |
| 6,746,667 B2 | 6/2004 | Badejo et al. | |
| 6,899,897 B2 | 5/2005 | Battaglia | |
| 8,709,439 B2 | 4/2014 | Battaglia et al. | |
| 2002/0004190 A1* | 1/2002 | Diasti et al. | 433/215 |

(Continued)

FOREIGN PATENT DOCUMENTS

| | | |
|---|---|---|
| EP | 0 128 655 A2 | 12/1984 |
| EP | 0 525 267 A2 | 2/1993 |

(Continued)

OTHER PUBLICATIONS

English et al., A Natural Approach to Reducing Gastritis, Ulcers and Stomach Cancer, Nutrition Reviews.*
Keller-Melchior, R. and W., Brauninger, "Allergic contact dermatitis from anthrarobia", *Contact Dermatitis*, 33:61, (1995).
Balanyk et al., "Development of Sustained-release Antimicrobial Dental Varnishes Effective Against *Streptococcus mutans* in vitro," Journal of Dental Research, vol. 64, pp. 1356-1360, 1985.
International Search Report issued on Feb. 10, 2003 in application No. PCT/US02/16434 (corresponding to U.S. Pat. No. 6,899,897).
International Search Report issued on Sep. 12, 2007 in application No. PCT/US06/43572.
Office Action issued on Jun. 22, 2011 in U.S. Appl. No. 12/091,043 (US 2008/0317690).
Office Action issued on Mar. 2, 2011 in U.S. Appl. No. 10/754,430 (US 2005/0095208).
Notice of Allowance issued on Jul. 23, 2004 in U.S. Appl. No. 10/053,313 (U.S. Pat. No. 6,899,897).

(Continued)

*Primary Examiner* — Lezah Roberts
(74) *Attorney, Agent, or Firm* — Foley & Lardner LLP

(57) ABSTRACT

The invention provides a biological dressing for treatment of a condition of the skin, mucosa, teeth or other tissue within or proximate to the oral cavity of a subject, the biological dressing comprised of a gum resin, a topically acceptable volatile solvent, and an oral care agent. The gum resin is present in a suitable amount that the composition, when the solvent evaporates, will dry to form a solid coating that sticks to the tissue to which the composition is applied and maintain the oral care agent over a sustained period of time in contact with sites on the tissue exhibiting symptoms of the condition. Methods are provided for treating symptoms of oral condition with such a oral care composition.

2 Claims, No Drawings

(56) References Cited

U.S. PATENT DOCUMENTS

| | | | |
|---|---|---|---|
| 2002/0018757 A1 | | 2/2002 | Harichian et al. |
| 2002/0082279 A1 | | 6/2002 | Schultz |
| 2002/0137728 A1 | * | 9/2002 | Montgomery .................. 514/99 |
| 2002/0185396 A1 | * | 12/2002 | Mainwaring et al. ........ 206/361 |
| 2003/0068331 A1 | | 4/2003 | Battaglia et al. |
| 2008/0286299 A1 | | 11/2008 | Battaglia |
| 2008/0317690 A1 | | 12/2008 | Battaglia |

FOREIGN PATENT DOCUMENTS

| | | | |
|---|---|---|---|
| EP | 0 428 520 B1 | | 9/1993 |
| EP | 0 923 937 A2 | | 6/1999 |
| GB | 981 144 A | | 1/1965 |
| JP | 59-216822 | * | 12/1984 |
| JP | 60-061518 | | 4/1985 |
| JP | 60-228412 | | 11/1985 |
| JP | 03-002126 | | 1/1991 |
| JP | 05-245172 | | 9/1993 |
| JP | 09-255565 | | 9/1997 |
| JP | 10-130173 | | 5/1998 |
| WO | WO 92/15289 | | 9/1992 |
| WO | WO 98/35709 | | 8/1998 |
| WO | WO 99/59405 | | 11/1999 |
| WO | WO 99/66870 | | 12/1999 |
| WO | WO 00/18380 | * | 4/2000 |

OTHER PUBLICATIONS

Office Action issued on Feb. 3, 2004 in U.S. Appl. No. 10/053,313 (U.S. Pat. No. 6,899,897).
Office Action issued on Jul. 15, 2003 in U.S. Appl. No. 10/053,313 (U.S. Pat. No. 6,899,897).
Office Action issued on Mar. 21, 2003 in U.S. Appl. No. 10/053,313 (U.S. Pat. No. 6,899,897).
Office Action issued on May 2, 2011 in U.S. Appl. No. 10/279,704 (US 2003/0068331).
Office Action issued on Jul. 28, 2010 in U.S. Appl. No. 10/279,704 (US 2003/0068331).
Office Action issued on Apr. 7, 2010 in U.S. Appl. No. 10/279,704 (US 2003/0068331).
Office Action issued on Jul. 2, 2009 in U.S. Appl. No. 10/279,704 (US 2003/0068331).
Office Action issued on Jan. 27, 2009 in U.S. Appl. No. 10/279,704 (US 2003/0068331).
Office Action issued on Aug. 11, 2008 in U.S. Appl. No. 10/279,704 (US 2003/0068331).
Office Action issued on May 12, 2008 in U.S. Appl. No. 10/279,704 (US 2003/0068331).
Office Action issued on Jul. 19, 2007 in U.S. Appl. No. 10/279,704 (US 2003/0068331).
Office Action issued on Mar. 13, 2007 in U.S. Appl. No. 10/279,704 (US 2003/0068331).
Office Action issued on Oct. 26, 2006 in U.S. Appl. No. 10/279,704 (US 2003/0068331).
Office Action issued on Aug. 25, 2004 in U.S. Appl. No. 10/279,704 (US 2003/0068331).
Bennet and Grist, "Nasal papillomas: successful treatment with podophyllin", South. Med. J., 78(2):224-225 (1985).
"Benzoinum" King's American Dispensatory, by Harvey Felter & John Lloyd, 1898 retrieved Jun. 16, 2003 from http://www.ibiblio.org/herbmed/eclectic/kings/styrax-benz.html.

Goh et al., "Comparing treatment response and complications between podophyllin 0.5%/0.25% in ethanol vs podophyllin 25% in tincture benzoin for penile warts", Singapore Med. J., 39(1):17-19 (1998).
Lim et al., "Self-application of podophyllin resin for penile condylomata acuminata", Ann. Acad. Med. Singap., 16(1):167-169 (1987).
Moher and Maurer, "Podophyllum toxicity: case report and literature review", The Journal of Family Practice, 9(2):237-240 (1979).
Ozumba & Megafu, "Pattern of vulval warts at the University of Nigeria Teaching Hospital, Enugu, Nigeria", Int. J. Gynaecol. Obstet., 34(4):347-352 (1991).
"PDR entry for Podocon-25 Liquid" from American health Consultants, Inc., 2001 retrieved Jun. 19, 2003 from http://www.ctciconsult.com/pdrdruginfo/html/61201000.htm.
"Podocon-25" Material Safety Data Sheet retrieved Jun. 19, 2003 from http://wwwpaddocklabs.com/forms/msds/podocon.pdf.
"Podocon-25" retrieved Jun. 16, 2003 from http://www.stanford.edu/group/virus/1999/thanatos/podophyillin.html.
"Podophyllum (Topical)" from Thomson MICROMEDEX, 2003 retrieved Jun. 19, 2003 from http://health.yahoo.com/health/drus/202469/_overview.html.
Reynolds et al., "An audit of treatment of genital warts: opening the feedback loop", Int. J. of STD & AIDS, 4(4):226-231 (1993).
Simmons P.D., "Podophyllin 10% and 25% in the treatment of ano-genital warts. A comparative double-blind study", Br. J. Vener. Dis., 57(3):208-209 (1981).
"Tinctura Benzoini" King's American Dispensatory, by Harvey Fetter & John Lloyd, 1898 retrieved Jun. 16, 2003 from http://www.ibiblio.org/herbmed/eclectic/kings/styraxbenz_tinc.html.
Venkatraman & Gale, "Skin adhesives and skin adhesion. 1. Transdermal drug delivery systems", Biomaterials, 19(13):1119-1136 (1998).
Office Action issued on Apr. 1, 2011 in U.S. Appl. No. 12/182,372 (US 2008/0286229).
Office Action issued on Mar. 8, 2012 in U.S. Appl. No. 12/182,372 (US 2008/0286229).
Office Action issued on Dec. 6, 2011 in U.S. Appl. No. 12/091,043 (US 2008/0317690).
Supplementary European Search Report EP 06 84 4298 dated Mar. 27, 2012.
Office action issued on Jun. 12, 2013 in U.S. Appl. No. 12/091,043 (US 2008/0317690).
Office action issued on Feb. 13, 2013 in U.S. Appl. No. 12/091,043 (US 2008/0317690).
Office action issued on Aug. 15, 2012 in U.S. Appl. No. 12/091,043 (US 2008/0317690).
Notice of Allowance issued on Dec. 16, 2013 in U.S. Appl. No. 12/182,372 (U.S. Pat. No. 8,709,439).
Office Action issued on Mar. 19, 2015 in U.S. Appl. No. 12/091,043 (US 2008/0317690).
Office Action issued on Jul. 7, 2014 in U.S. Appl. No. 12/091,043 (US 2008/0317690).
Lichtenberger et al., "Insight Into NSAID-Induced Membrane Alterations, Pathogenesis and Therapeutics: Characterization of Interaction of NSAIDS with Phosphatidylcholine," Biochim. Biophys Acta, vol. 1821, No. 7, pp. 994-1002, Jul. 2012.
Office Action issued on Oct. 2, 2015 in U.S. Appl. No. 12/091,042 (US 2008/0317690).
Fisher A.A. (1986) *Contact Dermatitis.* 169-170.
Hjorth N. (1961) Eczematous Allergy to Balsams. *Acta Dermatovenereologica* (suppl) 46:1-216.
Keller-Melchior, R., Brauninger, W. (1995) "Allergic contact dermatitis from anthrarobin"*Contact Dermatitis.* Nov:33:361.

* cited by examiner

ORAL CARE COMPOSITIONS FOR TOPICAL APPLICATION

RELATED APPLICATION DATA

This application claims priority under 35 U.S.C. §119(e) to U.S. Ser. No. 60/517,319, filed Nov. 3, 2003, which is herein incorporated by reference in its entirety.

BACKGROUND OF THE INVENTION

Field of the Invention

The invention relates to gum resin or other film forming agent based biological dressings that adhere to oral tissue, such as the skin, mucosa, teeth or other tissue surfaces of the oral cavity and contain one or more agents for the treatment of symptoms related to oral conditions, including conditions due to oral hygiene, and dental health and/or appearance.

Background Information

The prophylactic, therapeutic and cosmetic benefits of maintaining high standards in oral hygiene and dental health are widely known. These benefits include reduction in caries, plaque, gingivitis and tartar; treating hypersensitivity; freshening breath; whitening teeth and removing stains; re-mineralizing teeth and the like.

One major oral hygiene concern for many people is halitosis, which is commonly referred to as bad breath. Halitosis is the result of volatile sulfur compounds, carboxylic acids and amines, generated by certain oral bacteria, that build up in the oral cavity. Not only is halitosis unpleasant but its presence can be indicative of poor oral hygiene and can also be one of the first signs of some more severe underlying problems. This is because the build up of matter which causes the bad breath associated with halitosis can also lead to the formation of plaque, the origin of dental caries, gingivitis and dental calculus.

Cosmetic aspects of oral care, such as the appearance of bright or "white" teeth, are also highly valued. Unfortunately, many substances that a person confronts on a daily basis can stain or reduce the "whiteness" of one's teeth. In particular, many foods such as coffee or tea and tobacco products and fluids tend to stain one's teeth. Such products or substances accumulate on the enamel layer of the tooth and form a pellicle film over the teeth and permeate the enamel layer, thereby staining the teeth. This problem occurs gradually over many years, but imparts a noticeable discoloration of the enamel of one's teeth. Further, the natural aging process results in even slight discoloration of the tooth as compared over the course of time.

In addition to typical oral hygiene procedures, such as brushing and flossing, a wide variety of oral care products are available which aid the maintenance of good oral hygiene by delivering various oral care substances or agents to the soft and hard tissues of the oral cavity. In general, such products exist in a form that permit use by the consumer themselves either at-home or away from the home and/or are administered by dentists/hygienists as part of their professional routine of oral hygiene treatments.

For example, conventional tooth whitening is accomplished by using whitening products on the dentin, which is the main, calcareous part of a tooth, beneath the enamel and surrounding the pulp chamber and root canals. Conventional tooth-whitening solutions generally take the form of a gel or paste, and are typically applied in conjunction with a mouthpiece or tray that fits snuggly over the surface of the teeth. The tooth-whitening process takes many hours to achieve desired results. Drawbacks including discomfort and potential injury due to poorly fitting trays and long duration for minimal efficacy.

A substantial limitation of many of the commonly used oral care products, including whitening solutions, is their brief period of efficacy when applied to the oral tissues. For example, the low viscosities of many oral care products do not allow the active ingredients to remain in contact with the targeted surface for as long as is necessary to effect the condition being treated because of the constant flushing effects of salivary secretions. In addition, saliva contains high concentrations of enzymes that can decompose the active agents contained in many products. In the case of teeth whitening products, saliva, which contains the enzyme catalase, rapidly decomposes the tooth whitening agent peroxide contained in many whitening solutions into gaseous oxygen and water. As a result, there is only transitory contact of the peroxide whitening agent with the teeth. This tendency toward rapid decomposition of active ingredients and/or the rapid flushing away of the product applied to the oral surface causes poor delivery of the oral care agent to the desired location, including insufficient, uneven or disparate application; as well as inefficiency due to loss of the product. Accordingly, the efficiency and utility for these oral care products in maximizing both oral hygiene and cosmetic appearance is currently limited.

Therefore, there is a need for a clean and inexpensive vehicle/carrier of topically applied oral care agents that increases the convenience, efficiency and effectiveness of the treatment, and decreases inappropriate or disparate application of the agents. It is preferably associated with less waste and lower cost and ultimately leads to improved treatment of the oral conditions and increased user satisfaction.

SUMMARY OF THE INVENTION

Compositions and methods are provided for increasing the effectiveness of treatment of oral hygiene and/or oral cosmetic conditions in a mammal by using a gum resin or other film forming agent as a carrier for an oral care agent. The oral care compositions include a gum resin or other film forming agent, at least one topically acceptable oral care agent for treatment of an oral hygiene or cosmetic condition other than the gum resin or other film forming agent, and a topically acceptable volatile solvent. The methods of treating symptoms of a oral hygiene or cosmetic condition include the steps of contacting affected sites of a subject in need thereof with the composition having a gum resin or other film forming agent, an oral care agent or agents, and an evaporative solvent, and allowing it to dry to form a biological dressing. The biological dressing comprises a sticky film of gum resin or other agent, which forms a film on the skin, and an oral care agent; the latter remains on the site of application after the volatile solvent has evaporated from the resin or other film-forming composition. The dressing forms a hydrophobic, protective film that provides sustained release of the oral care agent at the site of application. The invention finds use in the treatment of oral hygiene conditions or oral cosmetic conditions such as discoloration of the teeth, plaque, tartar, cavity prevention and treatment, inflamed or bleeding gums, mucosal wounds or lesions, microbial proliferation, and the elimination of mouth odor, such as due to halitosis. Such discoloration may be due to natural aging, food stains, tobacco stains, and the like. It is not a requirement of the invention that the discoloration be of any particular level, as long as the subject desires an appearance of "whitening" of the teeth.

DETAILED DESCRIPTION OF THE INVENTION

Compositions and methods are provided for the convenient and effective prevention and/or treatment of at least one symptom of an oral hygiene or oral cosmetic condition in a mammal, particularly by application of a biological dressing having at least one oral care agent. The terms "biological dressing," "biologic dressing," "biologic bandage" or "oral care composition" are used interchangeable herein and are intended to include a non-occlusive but adherent composition that is formed by drying on the skin, mucosa, or other soft or hard tissues of the oral cavity, a composition comprised of a gum resin, such as benzoin or mastic gum or other composition that can form a barrier film at the site of application, such as compositions that are used as skin wound sealing agents, an oral care agent and topically acceptable volatile solvent, such as ethanol. The biologic dressing forms a protective coating at the site(s) on the tissue of the oral cavity exhibiting symptoms of the condition and also acts as a reservoir for the oral care agent(s) to provide sustained delivery of an appropriate agent or combination of agents to the site. The biological bandage is easily removed using a solvent such as ethanol. Since the coating that contains the agent(s) is easily distributed evenly and stays in place until such deliberate removal, the effectiveness of the treatment is increased. This also allows for a decreased treatment time, and, ultimately, improved treatment of symptoms and increased subject satisfaction. Thus, oral care compositions of the invention can be used to improve delivery of oral care agents that are typically applied topically for the treatment conditions related to oral hygiene or oral cosmetics, e.g., teeth whitening.

The oral care compositions of the present invention are useful for treating, regulating or preventing conditions related to oral hygiene or oral cosmetics. Examples of the "oral conditions", "oral hygiene", "cosmetic conditions", or "oral cosmetics" addressed herein include, but, are not limited to appearance and discoloration of the teeth, plaque, tartar, cavity prevention and treatment, inflamed and/or bleeding gums, mucosal wounds, lesions, ulcers, aphthous ulcers, cold sores tooth abscesses, halitosis, mouth odor, and microbial proliferation.

As used herein, "treating" or "regulating" oral hygiene or cosmetic condition includes prophylactically regulating or therapeutically treating the appearance and structural changes to teeth, whitening, stain bleaching, stain removal, plaque prevention and removal, tartar prevention and removal, cavity prevention and treatment, inflamed and/or bleeding gums, mucosal wounds, lesions, ulcers, aphthous ulcers, cold sores tooth abscesses, microbial proliferation, and the elimination of mouth odor resulting from halitosis and/or the conditions above.

The "tissue" or "oral tissue" particularly amenable to treatment with the compositions described herein include skin, mucosa, teeth, or other hard or soft tissue proximate to or within the buccal or oral cavity or vestibule. Oral tissues subject to application of the oral care compositions of the present invention therefore include the soft oral tissues such as skin or mucosa of the lips, cheeks, mouth, and gums, and hard tissues such as teeth, including, for example, the dentin, cementum, and enamel comprising the outer layer of the teeth.

Thus, the compositions of the present invention may contain one or more oral care agents. As used herein, the term "oral care agent" refers to any material that is generally considered as safe for use in the oral cavity that provides changes to the overall health, hygiene, and/or cosmetic appearance of the oral cavity, and specifically the condition of the oral surfaces the oral care substance contacts.

The advantages of the invention include a more specifically and evenly directed application of oral care agents to sites affected by a condition, and extended retention on the site of application of the agent because the film is resistant to water and fluids such as saliva. Additionally, the vehicle is relatively inexpensive, is pleasant smelling, and the bandage can be conveniently and easily removed, for example with alcohol, when desired. Many oral conditions are exacerbated by moisture, or application of an agent is dissipated by decomposition or flushing away by fluids such as saliva, so the water repellent qualities of the dressing also protect the tissue from further damage. The biological dressings are designed to be directly applied to an areas of tissue needing treatment, and left in place for an extended period of time, without requiring conventional adhesive bandages. It is intended that the dressing need only be washed from the area for purposes of convenience and cleanliness. The biological dressings of the subject invention are cleaner and easier to apply than conventional dressings and existing compositions, have less waste and are more economical, allowing for more efficient, efficacious and palatable relief of symptoms or recovery from the oral condition being treated.

Further advantages of the subject invention include that various of the gum resins that find use, including benzoin and mastisol, and wound sealing agents are already approved for human use and have been tested and found to be safe for topical application on non-human mammals; the wound sealing agents have the advantage of being able to deliver alcohol insoluble agents while reducing disparate distribution to the area of tissue where treatment is desired.

The biological dressings are prepared by drying on the tissue, a composition comprising an oral care agent that can be used to ameliorate the symptoms of a oral condition and a gum resin dissolved in a volatile solvent. Generally, the oral care composition is prepared as a sticky slurry or solution of the film forming agent and the oral care agent that can be applied to a site on the tissue. The consistency of the composition can be varied by adjusting the ratio of solvent to gum resin in the composition to achieve the desired consistency for application to a particular site. For areas where evaporation of solvent may be slower, it may be desirable to prepare the composition as a paste and to use a more volatile solvent, whereas for application to hard to reach areas, it may be desirable to prepare a less viscous composition that can be applied thinly to the affected areas. For those of the wound sealing agents that come in an un-polymerized or liquid form that, once in contact with tissue, develops into a dry adhesive layer or film, no solvent is generally necessary other than what may be necessary to properly blend in the oral care agent.

The relative proportions of the gum resin or other film forming agent, the oral care agent or agents, and the evaporative solvent in the preferred composition can vary widely, and depend upon the specific intended use of the biological dressing. Precise preferred ratios depend to some extent on the rate of release of the agent from the film, the desired stickiness of the residual film, and the area of application. For example, if the intended application is to an affected area on the face or the lips, the preferred composition would have a lower proportion of gum resin or other film forming agent, to allow for a more thinly applied and less visible and less sticky dressing. Generally, the compositions of the subject invention will have at least about 10% gum resin or other film forming agent, more likely about 20%, 30% or 40% gum resin or other film forming agent, and as much as 50% or 60% gum resin or other film forming agent.

The stickiness of the biological dressings is provided by the use of a gum resin or other film forming agent. The gum resins that are used generally are naturally occurring gum resins, such as those that are harvested from trees, although gum resins also may be prepared by synthetic means (see for example, U.S. Pat. Nos; 5,644,049, 5,429,590 and 4,307,717). Preferred gum resins include benzoin resinous exudate harvested from Styracaceae trees, including *Benzoin Siam* from *Styrax Tonkinesis* and *Behzoin Sumatra* from *Styrax Benzoin*. Tincture of benzoin and benzoin compound tincture is readily available through numerous commercial sources, including many drug stores and suppliers of surgical goods. Another resinous tree exudate that is preferred and is commonly used in the medical arts for enhancing the adherence of surgical bandages, is mastic gum, which is harvested from Pistacia lentiscus. A tincture of mastic gum (Mastisol) is produced by Ferndale Laboratories in Ferndale, Mich. and is also available through suppliers of surgical goods. Other gum resins that can be used include the gum resin exudates from Burserceae trees, including *Boswellia serrata* (also known as Boswellin), *Boswellia dalzielii, Boswellia carteri* (gum olibanum) and *Canarium luzonicum* or *Canarium commune* (Elemi gum or resin). Additional resinous exudates contemplated from other tree species include *Eucalyptus* species (*Eucalyptus globulus*) and *Myrtaceae* "Tea-tree" species (*Melaleuca alternifolia, Leptospermum scoparium,* and *Kunzea ericoides*). Many naturally occurring gum resins themselves have pharmacological properties, and their topical application may cause irritation in certain subjects or exacerbate certain conditions. Prudent choice of the gum resin to be used in preparing a particular biological dressing takes into consideration the condition to be treated and the sensitivities of a particular subject's tissue.

In addition to the gum resins, biologic dressings can be made from several classes of adhesive polymers including acrylic polymers (e.g. cyanoacrylates), polyisobutylenes and silicones. Examples of the acrylic polymers include acrylate-vinylacrylate, dimethylaminoethylmethacrylate, methacrylic esters, N-2-butylcyanoacrylate, 2-octylcyanoacrylate, polyacrylic acid, polyaminomethylmethacrylate and polymethlmethacrylate. Polyisobutylenes (a sub-type of polyolefins) are pressure sensitive adhesives made by blending multiple molecular weights to achieve desired adhesive and agent-carrier properties. Silicones are available in the form of gels, liquids, or elastomers, depending on the nature of side groups and the interchain cross-linking. Other potential adhesive vehicles include hydrogel polymers such as poly (oxypropylene-co-oxyethene) glycol, cellulose bioadhesives such as hydroxypropylmethyl-cellulose, synthetic laticies such as polyvinyl acetate and ethylene vinyl-acetate, mucosal adhesives such as polyoxyethylene, pyroxylin solutions, and the iodophors. Commercial sources of film forming agents that can be combined directly with a oral care agent include Dermabond (Ethicon) which is a formulation of 2-octylcyanoacrylate; Liquid Band Aid (Johnson and Johnson) which is also a formulation of 2-octylcyanoacrylate; Liquidenm, Soothe-N-Seal, Nexa Band ( all from Closure Medical Co), all formulations of cyanoacrylate; "New-Skin" (New Skin) containing pyroxylin; and hydrogels containing poly (oxypropylene-co-oxyethene) glycol (MedLogic).

A desirable feature of the subject compositions is that they form an adherent and protective film or biological bandage over a treatment area. To effect this attribute, the composition is prepared with a volatile solvent that evaporates to leave a hydrophobic coating comprised of the gum resin or other film forming agent and the oral care agent on the skin. Volatile solvents for use in the subject compositions include alcohols such as methanol, ethanol, propanol, and isopropanol, ketones, such as acetone, and ethers such as dimethyl ether. Other evaporative compounds may also find use, so long as they are compatible with other components of the composition and topically acceptable to the majority of subjects. The gum resin of choice is diluted in the volatile solvent such that the concentration of solvent comprises at least about 40% or 50% (v/v or v/w), more commonly at least about 60%, 70% or 80%, or as much as about 90% of the total composition. A particularly preferred composition is a tincture of benzoin, which acts as a skin protectant and is comprised of benzoin in about 60%, 70%, 80% or 90% ethanol in combination with small percentages of aloe, storax and tolu balsam.

Optionally, the biologic dressing may include a penetration enhancer, i.e., a chemical compound that, when included in a formulation, temporarily increases the permeability of the skin to a cosmetic agent allowing more of the agent to be absorbed in a shorter period of time. Examples of penetration enhancers that can be used include dimethylsulfoxide, n-decyl methyl sulfoxide, N,N-dimethylacetamide, N,N-methyl-2-pyrrolidone and octylphenylpolyethylene glycols. Other known dermal penetration enhancers include laurocapram (Azone.RTM.) and laurocapram derivatives, such as those 1-alkylazacycloheptan-2-ones specified in U.S. Pat. No. 5,196,410, and oleic acid and its ester derivatives, such as methyl, ethyl, propyl, isopropyl, butyl, vinyl and glycerylmonooleate, and sorbitan esters such as sorbitan monolaurate and sorbitan monooleate, and other fatty acid esters such as isopropyl laurate, isopropyl myristate, isopropyl palmitate, diisopropyl adipate, propylene glycol monolaurate and propylene glycol monooleate, and long chain alkyl esters of 2-pyrrolidone, particularly the 1-lauryl, 1-hexyl and 1--2-ethylhexyl) esters of 2-pyrollidone and those dermal penetration enhancers given in U.S. Pat. No. 5,082,866, particulary dodecyl (N,N-dimethylamino) acetate and dodecyl (N,N-dimethylamino) propionate and in U.S. Pat. No. 4,861,764, particularly 2-n-nonyl-1-3-dioxolane. Preferred known dermal penetration enhancers are laurocapram and laurocapram derivatives, such as those 1-alkylazacycloheptan-2-ones specified in U.S. Pat. No. 5,196,410, and oleic acid and its ester derivatives, such as methyl, ethyl, propyl, isopropyl, butyl, vinyl and glycerylmonooleate, and those given in U.S. Pat. No. 5,082,866, particularly dodecyl (N,N-dimethylamino) acetate and dodecyl (N,N-dimethylamino) propionate and in U.S. Pat. No. 4,861,764, particularly 2-n-nonyl-1-3-dioxolane. Most preferred known dermal penetration enhancers are oleic acid and its ester derivatives, such as methyl, ethyl, propyl, isopropyl, butyl, vinyl and glycerylmonooleate, and those given in U.S. Pat. No. 5,082,866, particulary dodecyl (N,N-dimethylamino) acetate and dodecyl (N,N-dimethylamino) propionate and in U.S. Pat. No. 4,861,764, particularly 2-n-nonyl-1-3-dioxolane.

The oral care agent or agents included in the compositions will depend upon the condition being treated. To allow for extended contact of the biological dressing with the area of tissue under treatment, oral care agents chosen should be efficacious without being locally or systemically toxic or caustic to the mammal to which the dressing is administered. (i.e., a "safe and effective amount")

The time of treatment, or time a biological dressing of the subject invention is intended to remain at the site of application, is based at lease in part upon the nature of the condition to be treated and the agent(s) that are being used. For example, the time of treatment may be less than one hour, 1-3 hours, at least 6 hours, as long as 8, 10 or 12 hours, sometimes as long as 16, 18 or 20 hours, and for certain treatments, as long as 24, 36 or 72 hours or even longer prior to removal. In general, the compositions are formulated so that the concentration of the oral care agent(s) that is in the biological bandage approximates the concentration of oral care agent that is used in existing topical formulations. However, because the adherent properties of a gum resin-based biological dressing allow for extended and continuous exposure of tissue to an agent, reduced concentration formulations are possible and even preferred. The amount to be used can therefore be adjusted as appropriate. Generally, the amount used will be within the range of ±25% of the indicated concentration, preferably within ±10% of the indicated concentrations. In the following paragraphs, the percentages appearing in parenthesis after the name of a particular agent represent the concentration(s) of agent that is(are) used in existing topical formulations.

Oral care compositions or substances of the present invention may include many of the agents previously disclosed in the art. In any embodiment of the present invention, however, the oral care agents useful herein can be categorized by the benefit they provide or by their postulated mode of action. However, it is to be understood that the agents useful herein can in some instances provide more than one benefit or operate via more than one mode of action. Therefore, classifications herein are made for the sake of convenience and are not intended to limit the agent to that particular application or applications listed.

Teeth Whitening Agents

Teeth whitening agents may be included in the oral care compositions of the present invention. Non-limiting examples of agents suitable for whitening include peroxides, metal chlorites, perborates, percarbonates, peroxyacids, and combination thereof. Suitable peroxide compounds include, for example, hydrogen peroxide, calcium peroxide, carbamide peroxide, and mixtures thereof. Suitable metal chlorites include calcium chlorite, barium chlorite, magnesium chlorite, lithium chlorite, sodium chlorite, and potassium chlorite. Additional whitening actives may be hypochlorite and chlorine dioxide. Many teeth whitening agents are well known and are commercially available solutions in varying strength, for instance some peroxides are available in strengths from 35 to 70%. The concentration in the compositions of the invention would vary in accordance with the strength used. Therefore, the weight percent of the whitening active in the composition would be adjusted to account for the strength of the agent used, as may be appreciated by one skilled in the art.

Anti-Tartar Agents/Phosphates

Anti-tartar agents known for use in dental care products includes phosphates. Phosphates include pyrophosphates, polyphosphates, polyphosphonates and mixtures thereof. Pyrophosphates are well known for use in dental care products. Pyrophosphate ions are delivered to the teeth derive from pyrophosphate salts. The pyrophosphate salts useful in the present compositions include the di-alkali metal pyrophosphate salts, tetra-alkali metal pyrophosphate salts, and mixtures thereof. Disodium dihydrogen pyrophosphate, tetrasodium pyrophosphate, and tetrapotassium pyrophosphate in their unhydrated as well as hydrated forms may be used in the compositions provided herein. The pyrophosphate salts are described in more detail in Kirk & Othmer, Encyclopedia of Chemical Technology, Third Edition, Volume 17, Wiley-Interscience Publishers (1982), incorporated herein by reference in its entirety, including all references incorporated into Kirk & Othmer.

Agents that may be used in place of or in combination with the pyrophosphate salt include such known materials as synthetic anionic polymers including polyacrylates and copolymers of maleic anhydride or acid and methyl vinyl ether (e.g., Gantrez), as described, for example, in U.S. Pat. No. 4,627,977, to Gaffar et al., the disclosure of which is incorporated herein by reference in its entirety; as well as, e.g., polyamino propoane sulfonic acid (AMPS), zinc citrate trihydrate, polyphosphates (e.g., tripolyphosphate; hexametaphosphate), diphosphonates (e.g., EHDP; AHP), polypeptides (such as polyaspartic and polyglutamic acids), and mixtures thereof.

Fluoride Ion Source

Fluoride ion sources are well know for use in oral care compositions as anticaries agents. Fluoride ions are contained in a number of oral care compositions for this purpose, for example in toothpastes. Patents disclosing such toothpastes include U.S. Pat. No. 3,538,230, Nov. 3, 1970 to Pader et al; U.S. Pat. No. 3,689,637, Sep. 5, 1972 to Pader; U.S. Pat. No. 3,711,604, Jan. 16, 1973 to Colodney et al; U.S. Pat. No. 3,911,104, Oct. 7, 1975 to Harrison; U.S. Pat. No. 3,935,306, Jan. 27,1976 to Roberts et al; and U.S. Pat. No. 4,040,858, Aug. 9, 1977 to Wason.

Application of fluoride ions to dental tissue, such as enamel, serves to protect teeth against decay. A wide variety of fluoride ion-yielding materials can be employed as sources of soluble fluoride in the instant compositions. Examples of suitable fluoride ion-yielding materials are found in Briner et al; U.S. Pat. No. 3,535,421; issued Oct. 20, 1970 and Widder et al; U.S. Pat. No. 3,678,154; issued Jul. 18, 1972, both patents being incorporated herein by reference. Examples of fluoride ion sources for use herein include sodium fluoride, potassium fluoride and ammonium fluoride. The instant compositions provide from about 50 ppm to 10,000 ppm, more preferably from about 100 to 3000 ppm, of fluoride ions in the aqueous solutions that contact dental surfaces when used with the composition used in the mouth.

Antimicrobial Agents

Antimicrobial agents can also be present in the oral care compositions of the present invention. Such agents may include, but are not limited to, 5-chloro-2-(2,4-dichlorophenoxy)-phenol, commonly referred to as triclosan, and described in The Merck Index, 11th ed. (1989), pp. 1529 (entry no. 9573) in U.S. Pat. No. 3,506,720, and in European Patent Application No. 0,251,591 of Beecham Group, PLC, published Jan. 7, 1988; phthalic acid and its salts including, but not limited to those disclosed in U.S. Pat. No. 4,994,262, Feb. 19, 1991, substituted monoperthalic acid and its salts and esters as disclosed in U.S. Pat. No. 4,990,329, Feb. 5, 1991, U.S. Pat. No. 5,110,583, May 5, 1992 and U.S. Pat. No. 4,716,035, Dec. 29, 1987, all to Sampathkumar; preferably magnesium monoperoxy phthalate, chlorhexidine (Merck Index, no. 2090), alexidine (Merck Index, no. 222; hexetidine (Merck Index, no. 4624); sanguinarine (Merck Index, no. 8320); benzalkonium chloride (Merck Index, no. 1066); salicylanilide (Merck Index, no. 8299); domiphen bromide (Merck Index, no. 3411); cetylpyridinium chloride (CPC) (Merck Index, no. 2024; tetradecylpyridinium chloride (TPC); N-tetradecyl-4-ethylpyridinium chloride (TDEPC); octenidine; delmopinol, octapinol, and other piperidino derivatives; nicin preparations; zinc/stannous ion agents; antibiotics such as augmentin, amoxicillin, tetracycline, doxycycline, minocycline, and metronidazole; and analogs and salts of the above; essential oils including thymol, geraniol, carvacrol, citral, hinokitiol, eucalyptol, catechol (particularly 4-allyl catechol) and mixtures thereof; methyl salicylate; hydrogen peroxide; metal salts of chlorite and mixtures of all of the above.

Other examples of antibacterial and antifungal agents include B-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, phenoxy propanol, phenoxyisopropanol, capreomycin, chlorhexidine, chlortetracycline, oxytetracycline, clindamycin, ethambutol, hexamidine isethionate, pentamidine, gentamicin, kanamycin, lineomycin, methacycline, methenamine, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, ketaconazole, amanfadine hydrochloride, amanfadine sulfate, octopirox, parachlorometa xylenol, nystatin, tolnaftate, zinc pyrithione and clotrimazole.

Anti-Inflammatory Agents

Anti-inflammatory agents can also be present in the oral care compositions of the present invention. Such agents may include, without limitation, non-steroidal anti-inflammatory agents or NSAIDs such as ketorolac, flurbiprofen, ibuprofen, naproxen, indomethacin, aspirin, ketoprofen, piroxicam and meclofenamic acid. Use of NSAIDs such as Ketorolac are claimed in U.S. Pat. No. 5,626,838, issued May 6, 1997, herein incorporated by reference. Disclosed therein are methods of preventing and, or treating primary and reoccurring squamous cell carcinoma of the oral cavity or oropharynx by topical administration to the oral cavity or oropharynx an effective amount of an NSAID.

Nutrients

Nutrients may improve the condition of the oral cavity and can be included in the oral care compositions of the present invention. Nutrients include minerals, vitamins, oral nutritional supplements, enteral nutritional supplements, and mixtures thereof.

Examples of minerals that can be included with the compositions of the present invention include calcium, phosphorus, fluoride, zinc, manganese, potassium and mixtures thereof. These minerals are disclosed in Drug Facts and Comparisons (loose leaf drug information service), Wolters Kluer Company, St. Louis, Mo., ©1997, pp 10-17; incorporated herein by reference.

Vitamins can be included with minerals or used separately. Vitamins include, for example, Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Such vitamins are disclosed in Drug Facts and Comparisons (loose leaf drug information service), Wolters Kluer Company, St. Louis, Mo., ©1997, pp. 3-10; incorporated herein by reference.

Oral nutritional supplements include amino acids, lipotropics, fish oil, and mixtures thereof, as disclosed in Drug Facts and Comparisons (loose leaf drug information service), Wolters Kluer Company, St. Louis, Mo., ©1997, pp. 54-54e; incorporated herein by reference. Amino acids include, but, are not limited to L-Tryptophan, L-Lysine, Methionine, Threonine, Levocamitine or L-camitine and mixtures thereof. Lipotropics include, but, are not limited to choline, inositol, betaine, linoleic acid, linolenic acid, and mixtures thereof. Fish oil contains large amounts of Omega-3 (N-3) Polyunsaturated fatty acids, eicosapentaenoic acid and docosahexaenoic acid.

Entenal nutritional supplements include, but, are not limited to protein products, glucose polymers, corn oil, safflower oil, medium chain triglycerides as disclosed in Drug Facts and Comparisons (loose leaf drug information service), Wolters Kluer Company, St. Louis, Mo., ©1997, pp. 55-57; incorporated herein by reference.

Enzymes

An individual or combination of several compatible enzymes can be included in the oral care composition of the present invention. Enzymes are biological catalysts of chemical reactions in living systems. Enzymes combine with the substrates on which they act forming an intermediate enzyme-substrate complex. This complex is then converted to a reaction product and a liberated enzyme which continues its specific enzymatic function.

Enzymes provide several benefits when used for cleansing of the oral cavity. For example, proteases break down salivary proteins which are absorbed onto the tooth surface and form the pellicle; the first layer of resulting plaque. Proteases along with lipases destroy bacteria by lysing proteins and lipids which form the structural component of bacterial cell walls and membranes. Dextranases break down the organic skeletal structure produced by bacteria that forms a matrix for bacterial adhesion. Proteases and amylases, not only present plaque formation, but also prevent the development of calculus by breaking-up the carbohydrate-protein complex that binds calcium, preventing mineralization.

Non-limiting examples of enzymes useful in the present invention include any of the commercially available proteases, glucanohydrolases, endoglycosidases, amylases, mutanases, lipases and mucinases or compatible mixtures thereof. Examples more particularly include the proteases, dextranases, endoglycosidases and mutanases, even more particularly including papain, endoglycosidase or a mixture of dextranase and mutanase. Additional enzymes suitable for use in the present invention are disclosed in U.S. Pat. No. 5,000,939 to Dring et al., Mar. 19, 1991; U.S. Pat. No. 4,992,420 to Neeser, Feb. 12, 1991; U.S. Pat. No. 4,355,022 to Rabussay, Oct. 19, 1982; U.S. Pat. No. 4,154,815 to Pader, May 15, 1979; U.S. Pat. No. 4,058,595 to Colodney, Nov. 15, 1977; U.S. Pat. No. 3,991,177 to Virda et al., Nov. 9, 1976 and U.S. Pat. No. 3,696,191 to Weeks, Oct. 3, 1972; all incorporated herein by reference.

Antioxidants

Antioxidants are generally recognized as useful in oral care products and can be included in the oral care composition of the present invention. Antioxidants are disclosed in texts such as Cadenas and Packer, The Handbook of Antioxidants, ©1996 by Marcel Dekker, Inc., incorporated herein by reference. Antioxidants that may be included in the oral care composition or substance of the present invention include, but are not limited to Vitamin E, ascorbic acid, Uric acid, carotenoids, Vitamin A, flavonoids and polyphenols, herbal antioxidants, melatonin, aminoindoles, lipoic acids and mixtures thereof.

Flavoring Agent

The oral care composition of the present invention may also contain an agent added for enhancing flavor. Flavoring agents that are used in the practice of the present invention include essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Of these, the most commonly employed are the oils of peppermint, spearmint and wintergreen.

Fragrance

The oral care composition can optionally include a fragrance. As used herein, a "fragrance" refers to substance having an odor or a scent detectable to a mammal (e.g., human) and can "freshen" breath. Specifically, the fragrance can be a floral scent, a food scent, a fruit scent, a plant leaf scent, or any combination thereof.

The fragrance can be a low odor fragrance, a high odor fragrance, or a mixture thereof. The fragrance can be produced from a single compound or from a mixture of two or more compounds. In some instances a flavoring agent (see above) will also provide a desired fragrance. The fragrance can be present in any suitable and effective amount, e.g., up to about 10% of the oral care composition, up to about 1.0% of the composition, or up to about 0.1% of the oral care composition.

Mouth and Throat Products

Other materials that can be used with the present invention include commonly known mouth and throat products. Such products are disclosed in Drug Facts and Comparisons (loose leaf drug information service), Wolters Kluer Company, St. Louis, Mo., ©1997, pp. 520b-527; incorporated herein by reference. These products include, but, are not limited to anti-fungal, antibiotic and analgesic agents.

Preferred volatile liquids of the present invention include safe skin-tolerant solvents such as ethanol and isopropanol, although ethanol is preferred where ingestion of the solvent is likely. An aerosol propellant, such as dimethyl ether, may constitute a volatile liquid for the purpose of the present invention.

The biologic dressing may also include other acceptable carriers as needed that do not adversely affect the effectiveness of the agent, or the resinous delivery vehicle and do not damage the tissue to which it is applied. Suitable carriers include sterile water; saline, dextrose; dextrose in water or saline; condensation products of castor oil and ethylene oxide combining about 30 to about 35 moles of ethylene oxide per mole of castor oil; liquid acid; lower alkanols; oils such as corn oil; peanut oil, sesame oil and the like, with emulsifiers such as mono- or di-glyceride of a fatty acid, or a phosphatide, e.g., lecithin, and the like; glycols; polyalkylene glycols; aqueous media in the presence of a suspending agent, for example, sodium carboxymethyl-cellulose; sodium alginate; poly(vinyl pyrrolidone); and the like, alone, or with suitable dispensing agents such as lecithin; polyoxyethylene stearate; and the like. The carrier may also contain adjuvants such as preserving stabilizing, wetting, emulsifying agents and the like.

The oral care compositions of the invention can be administered alone or in conjunction with another device, such as a mouthpiece or tray that fits over the surface of the teeth.

For aerosol administration, the oral care compositions are preferably supplied in finely divided form together with a surfactant and propellant as pharmaceutically acceptable carriers. The surfactant is nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides, can be employed.

In practicing a method of treating the oral tissue of a subject, the oral care composition in its original prepared form, is applied directly and specifically on the lesions or other areas of the tissue requiring treatment. The biological dressing composition may initially be prepared in any form suitable for topical application, such as a paste, a liquid, a semi-solid, a gel, a suspension, an emulsion or the like, provided that the formulation allows the gum resin or other film forming agent carrier and oral care agent to effectively adhere together to the tissue surface to which they are applied and to form a protective barrier over the tissue once the volatile solvent has evaporated. To minimize waste, application is generally carried out by optionally, first drying the affected site, painting, dabbing or swabbing (and the like) the composition at the affected site or sites, but certain preparations can also be applied by spraying on the formulation, and allowing it to dry.

The biologic dressing composition can be applied wherever the subject has a oral condition for which treatment is desired. After application, the volatile solvent evaporates to leave a protective solidified, adherent and hydrophobic film or coating on the tissue surface to which it has been applied. The solidified film residue comprises the gum resin or other film forming agent carrier, and the oral care agent or agents. By forming a barrier holding the oral care agent to the surface, the gum resin or other film forming agent permits a sustained, continuous release and a prolonged exposure to the agent or agents. Continuous exposure of the oral tissue to the agent(s) is maintained as long as the coating stays in place. The biologic dressing, therefore can effect symptomatic relief with less frequent applications. For most oral conditions treated using a gum resin or other film forming agent-based dressing, one or two daily applications will be sufficient to promote-alteration, regression, or disappearance of the targeted condition. For certain less respondent conditions, three daily applications may be required to effect disappearance of symptoms. Other oral conditions may require application every second day to realize symptomatic relief. The composition conveniently can be removed at will, by application of an appropriate solvent, normally ethanol. The composition can also be removed by scrubbing with soap and water.

The invention compositions can be provided for use in one or more applications. For treatment with oral care composition comprising an agent identified as one which is effective in treating the symptoms of a oral condition amendable to treatment by application of oral care agent, the subject compositions can be provided as kits for use in one or more doses. The kits include containers which can also constitute a delivery system, holding a composition comprising an effective agent either as concentrates (including lyophilized compositions), which may be further diluted prior to use or they may be provided at the concentration of use, where the containers may include one or more dosages. Conveniently, in the kits single dosages can be provided in sterile containers so that the physician or the subject may employ the containers directly, where the containers have the desired amount and concentration of agents. When the containers contain the formulation for direct use, usually there will be no need for other reagents for use with the method. The kits also can be in the form of a system for single or multiple applications. For example, in the case of teeth whitening, the kit can contain from 2-15 applicators, for example, to include treatment over 2-15 days, e.g., 2 weeks. Accordingly, the kit includes sufficient oral care agent (e.g., whitener) for the same time period. The containers are made of plastic, glass, metal or such material deemed appropriate for each particular medication and can be light opaque as required for light sensitive formulations. The containers can be color-coded, each color being unique to a particular product and its respective active ingredient. The containers can also be color coordinated with the outer packaging to simplify marketing and consumer purchasing. Examples of containers that are also delivery systems are those that facilitate application of the subject compositions to the skin, mucosa, teeth or other tissues in or proximate to the oral cavity. The delivery systems can be any of a wide assortment of types of applicators (e.g. bottles), shapes and sizes of containers such as roll-on, spray with either a manual or aerosolized delivery system, applicators with small padded applicator tips for the delivery of buccal mucosal medications or syringe type applicators for semi-solid medication such as are described in U.S. Pat. No. 5,531,703 and references cited therein.

The invention compositions can be contained in packaging material, which comprises a label indicating that the subject compositions can be used to treat oral conditions in humans. In addition, instructions are typically included. in the kits of the invention.

The invention now being generally described, it will be more readily understood by reference to the following examples which are included for purposes of illustration only and are not intended to limit the present invention.

EXAMPLE 1

Treatment of Tinea Pedis

This example illustrates the treatment of Athlete's Foot (Tinea Pedis) with a Gum Resin-Based Biological Dressing Comprised of Tinture of *Benzoin* and *Clotrimazole*.

Tincture of benzoin compositions are produced with standard tincture of benzoin (3M, Minneapolis, Minn.). Replicated experiments were performed with a composition comprising tincture of benzoin with 60% alcohol plus 1% clotrimazole. To determine efficacy in treating athlete's foot, the benzoin/clotrimazole composition was applied to cases of athlete's foot, replicated 25 times. In each replicate, the composition led to complete clearance of the athlete's foot within 7 to 10 days, when applied once daily for 7 days. Tests were also replicated successfully on 9 other individuals. No allergic reaction was noted in this test, although the alcohol component reportedly led to stinging when applied to deep fissures. Minimal lint from the socks was noted on the coating where the composition was applied but was easily removed with ethanol. Efficacy of the benzoin/clotrimazole composition was compared to controls of tincture of benzoin alone and no treatment. The benzoin/clotrimazole composition provided symptomatic relief and led to healing more quickly than tincture of benzoin alone, though tincture of benzoin alone improved symptoms and signs more quickly when compared to no treatment. This is likely due to the fact that the sticky coating from the tincture tends to repel moisture. Efficacy of the benzoin/clotrimazole composition also was compared to commercially available medications such as Lamisil®, Lotrimin®, Mycelex®, and Tinactin®. In comparison, the benzoin/clotrimazole composition greatly decreased the time necessary for treatment compared to formulations of each of the commercial medications, particularly when the commercial medications were administered in the form of powder, liquid, solution, spray or gel. The benzoin/clotrimazole composition also decreased the time necessary for treatment when compared to cream versions of the above medications and was much less messy than any of the commercial preparations tested. Ongoing tests with benzoin/1% terbinafine combinations indicate that efficacy is increased up to 200% over Lamisil AT. Ongoing tests also indicate a 0% incidence of allergic reaction tested on 25 individuals receiving a benzoin/bacitracin preparation.

The above results demonstrate the improved symptomatic relief from a dermatological disorder that can be achieved by administering a topically acceptable agent in a gum resin carrier that forms a biological bandage in comparison presently available carriers. With a gum-resin-based biological dressing, relief from the unpleasant symptoms associated with a dermatological condition is realized more efficiently and in a more convenient and palatable manner.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporate by reference.

Although the invention has been described with reference to the above example, it will be understood that modifications and variations are encompassed within the spirit and scope of the invention. Accordingly, the invention is limited only by the following claims.

What is claimed is:

1. A topical composition comprising:
 a) mastic gum:
 b) a non-steroidal anti-inflammatory agent selected from the group consisting of ketorolac, flurbiprofen, ibuprofen, naproxen, idomethacin, aspirin, ketoprofen, piroxicam, and meclofenamic acid: and
 c) a topically acceptable volatile solvent selected from ethanol and isopropanol, wherein the topically acceptable volatile solvent comprises about 60% to 90% of said composition.

2. The composition according to claim 1, further comprising an essential oil or flavoring aldehyde, ester, or alcohol.

* * * * *